(12) United States Patent
Itoi

(10) Patent No.: US 7,585,276 B2
(45) Date of Patent: Sep. 8, 2009

(54) ENDOSCOPE SYSTEM AND OPERATION METHOD FOR ENDOSCOPE

(75) Inventor: Hiromu Itoi, Saitama (JP)

(73) Assignee: Fujinon Corporation, Saitama-Shi (JP)

( * ) Notice: Subject to any disclaimer, the term of this patent is extended or adjusted under 35 U.S.C. 154(b) by 708 days.

(21) Appl. No.: 11/068,433

(22) Filed: Mar. 1, 2005

(65) Prior Publication Data

US 2005/0222500 A1    Oct. 6, 2005

(30) Foreign Application Priority Data

Mar. 1, 2004   (JP)   ............................. 2004-056219
Nov. 5, 2004   (JP)   ............................. 2004-322799

(51) Int. Cl.
*A61B 1/00*   (2006.01)
*A61B 1/04*   (2006.01)
*A61B 1/06*   (2006.01)

(52) U.S. Cl. ...................................... 600/180; 600/113

(58) Field of Classification Search ......... 600/114–116, 600/160, 178–181, 113; 348/68–69
See application file for complete search history.

(56) References Cited

U.S. PATENT DOCUMENTS

| | | | |
|---|---|---|---|
| 4,040,413 A * | 8/1977 | Ohshiro | ...................... 600/116 |
| 4,622,584 A | 11/1986 | Nagasaki et al. | |
| 5,196,928 A * | 3/1993 | Karasawa et al. | ............. 348/65 |
| 5,398,056 A | 3/1995 | Yabe et al. | |
| 5,840,013 A * | 11/1998 | Lee et al. | ..................... 600/114 |
| 2002/0077593 A1* | 6/2002 | Perkins et al. | ........... 604/96.01 |
| 2003/0187330 A1* | 10/2003 | Abe | ............................ 600/180 |
| 2004/0015150 A1* | 1/2004 | Zadno-Azizi | ............... 604/523 |
| 2004/0186349 A1* | 9/2004 | Ewers et al. | ................ 600/114 |
| 2007/0010785 A1* | 1/2007 | Sekiguchi et al. | ........ 604/95.03 |

FOREIGN PATENT DOCUMENTS

| | | |
|---|---|---|
| JP | 10-248794 | 9/1998 |
| JP | 2000-356749 | 12/2000 |
| JP | 2001-340462 | 12/2001 |
| JP | 2002-98913 | 4/2002 |
| JP | 2002-301019 | 10/2002 |

* cited by examiner

*Primary Examiner*—John P Leubecker
*Assistant Examiner*—Philip R Smith
(74) *Attorney, Agent, or Firm*—Young & Thompson

(57) ABSTRACT

According to the endoscope system of the present invention, when the image pickup device of the first endoscope device detects illumination light irradiated from the illumination device of the second endoscope device, the control device performs control so as to reduce light quantity of the illumination device of the second endoscope device based on the level of luminance signal outputted from the solid state image pickup element of the image pickup device, and when the image pickup device of the second endoscope device detects illumination light irradiated from the illumination device of the first endoscope device, the control device performs control so as to reduce light quantity of the illumination device of the first endoscope device based on the level of luminance signal outputted from the solid state image pickup element of the image pickup device.

1 Claim, 7 Drawing Sheets

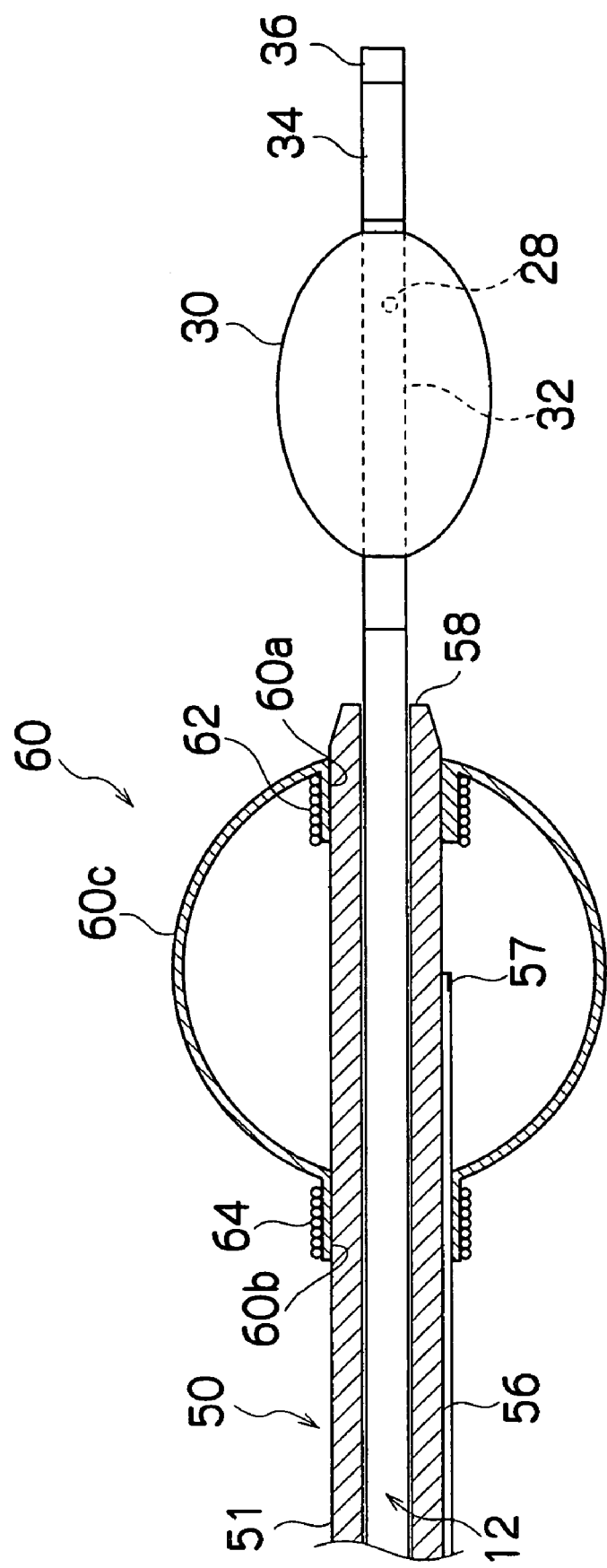

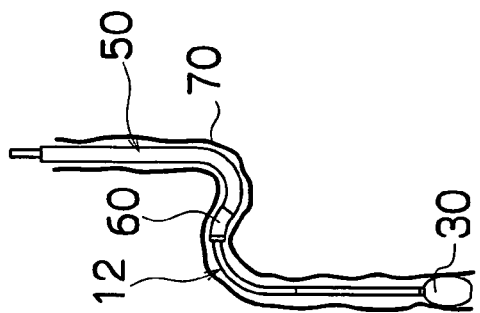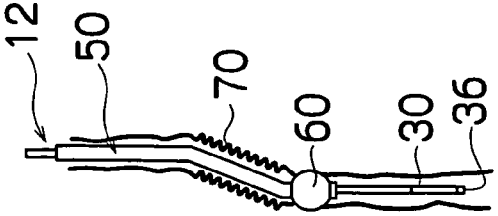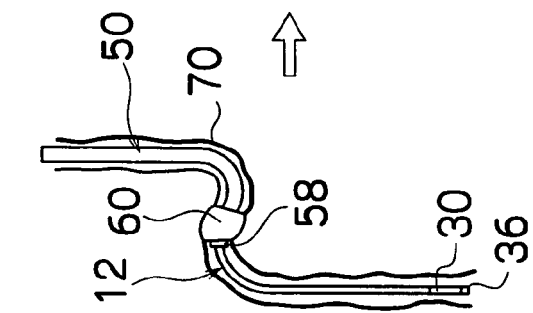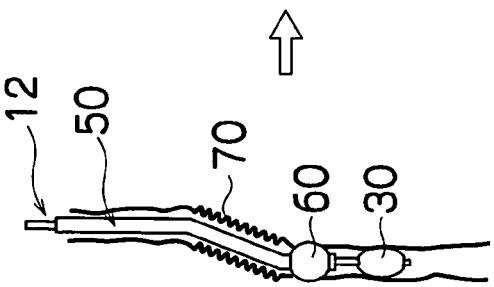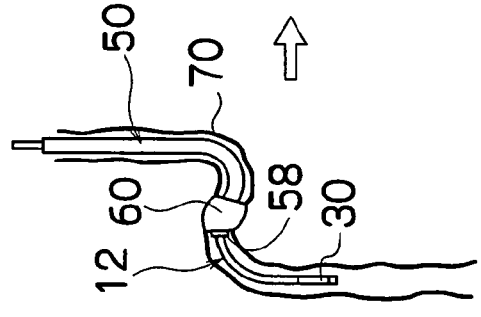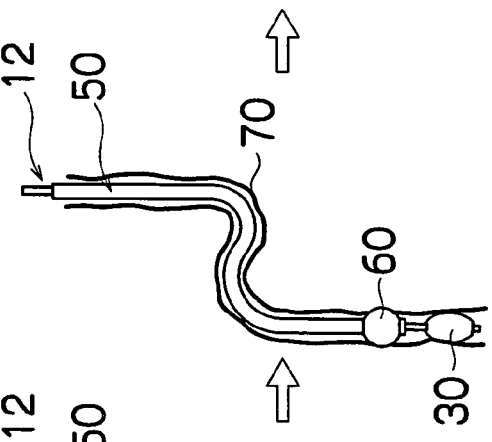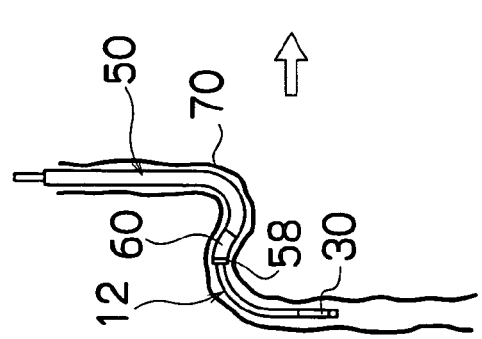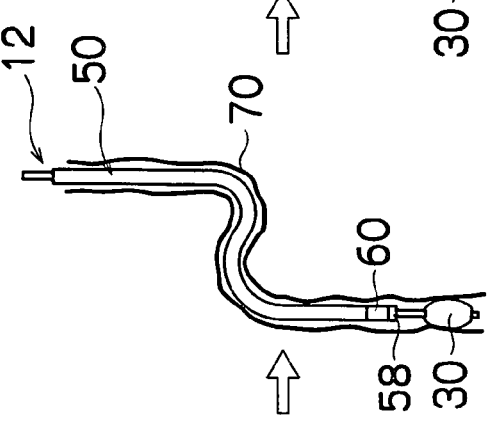

ENDOSCOPE SYSTEM AND OPERATION METHOD FOR ENDOSCOPE

BACKGROUND OF THE INVENTION

1. Field of the Invention

The present invention relates to an endoscope system and an operation method for the endoscope, and more particularly to an endoscope system comprising two endoscope devices, each having an endoscope provided with a balloon at the tip of an insertion part of the endoscope and having an insertion assisting tool for guiding the insertion part of the endoscope into a body cavity, the two endoscope devices being simultaneously inserted into the body cavity at the time of use, and to an operation method of the endoscopes.

2. Description of the Related Art

As kinds of endoscopes, there are, for example, a small intestine endoscope, a large intestine endoscope, etc. In the case of the small intestine endoscope, an insertion part is inserted from the mouth of a patient through the esophagus, the stomach and the duodenum into the small intestine, and in the case of the large intestine endoscope, the insertion part is inserted from the anus through the rectum into the large intestine, thereby predetermined treatment being performed in the respective cases.

However, when the insertion part of the endoscope is inserted into a deep part of the digestive tract, such as the small intestine, it is difficult to perform the insertion into the deep part by merely successively pushing the insertion part because complicated bent and sagged states of the intestine make the pushing force hardly transmittable to the tip of the insertion part. Accordingly, there is proposed an endoscope system in which an insertion assisting tool referred to as an overtube or a sliding tube, which is fitted to the insertion part of the endoscope, is inserted into a body cavity so as to guide the insertion part, thereby preventing excessive bending and deflection of the insertion part (for example Japanese Patent Application Laid-open No. 10-248794).

In the conventional endoscope system, there is also known an endoscope system of double balloon type, in which each of the tip part of an endoscope and the tip part of an insertion assisting tool is provided with a balloon (for example Japanese Patent Application Laid-open No. 2001-340462 and No. 2002-0301019).

SUMMARY OF THE INVENTION

However, in the case where a small intestine endoscope and a large intestine endoscope are simultaneously inserted so as to treat a same diseased part, there is an disadvantage that when illumination light from an illumination device of an endoscope device enters into the observation field of the opposing endoscope, a solid state image pickup element of the opposing endoscope is saturated due to the high-luminance of the illumination light, so as to cause only a white picture to be displayed on a monitor in such a manner that halation is generated, as a result of which a necessary observation image cannot be displayed.

The present invention has been made in view of the above described circumstances. An object of the present invention is to provide an endoscope system in which two endoscope devices are used for treating a same diseased part, and which is capable of displaying a good observation image on a display device without each endoscope device being influenced by the illumination light of the other endoscope device, and to provide an operation method for the endoscopes.

In order to achieve the above object, according to the present invention, there is provided an endoscope system, comprising: a first endoscope device provided with an endoscope, in which an illumination device, an image pickup device and a first balloon are attached to the tip part of an insertion part of the endoscope, and with an insertion assisting tool into which the insertion part of the endoscope is inserted, which assists insertion of the insertion part into a body cavity, and to the tip part of which a second balloon is attached; a second endoscope device provided with an endoscope in which an illumination device, an image pickup device and a first balloon are attached to the tip part of an insertion part of the endoscope, and with an insertion assisting tool into which the insertion part of the endoscope is inserted, which assists insertion of the insertion part into a body cavity, and to the tip part of which a second balloon is attached; a display device for displaying an object image photographed by the image pickup device of each of the first endoscope device and the second endoscope device; and a control device for controlling light quantity of either of the illumination devices, based on a level of luminance signal outputted from a solid state image pickup element of the image pickup device of the first endoscope device, when the image pickup device detects illumination light irradiated from the illumination device of the second endoscope device, or based on a level of luminance signal outputted from a solid state image pickup element of the image pickup device of the second endoscope device, when the image pickup device detects illumination light irradiated from the illumination device of the first endoscope device.

According to a first aspect of the present invention, in the case of treating a same diseased part by means of the first and second endoscope devices, when the image pickup device of the first endoscope device detects illumination light irradiated by the illumination device of the second endoscope device, the control device performs control so as to reduce light quantity of the illumination device of the second endoscope device based on the level of luminance signal outputted from the solid state image pickup element of the image pickup device. Also, when the image pickup device of the second endoscope device detects illumination light irradiated by the illumination device of the first endoscope device, the control device performs control so as to reduce light quantity of the illumination device of the first endoscope device based on the level of luminance signal outputted from the solid state image pickup element of the image pickup device. Accordingly, a good observation image can be displayed on the display device without each endoscope device being influenced by the illumination light of the other endoscope device.

According to a second aspect of the present invention, the control device is characterized in that the control device performs control so as to reduce light quantity of the second endoscope device when the luminance signal level from the solid state image pickup element of the first endoscope device reaches a saturation luminance signal level, or so as to reduce light quantity of the first endoscope device when the luminance signal level from the solid state image pickup element of the second endoscope device reaches a saturation luminance signal level.

According to the second aspect of the present invention, the light quantity is controlled based on the saturation luminance signal level of the solid state image pickup element, so that an observation image displayed on the display device is not whitened and is excellently displayed.

According to a third aspect of the present invention, there is provided an operation method of endoscopes which comprises a first endoscope device provided with an endoscope and an insertion assisting tool into which an insertion part of the endoscope is inserted and which assists insertion of the insertion part into a body cavity, and a second endoscope device provided with an endoscope and an insertion assisting tool into which an insertion part of the endoscope is inserted and which assists insertion of the insertion part into a body cavity, comprising the steps of: inserting the first endoscope device from the mouth of a patient; and inserting the second endoscope device from the anus of the patient, wherein treatment is performed by means of the first and second endoscope devices.

A fourth aspect according to the present invention, in the third aspect, includes an expandable and contractible first balloon which is provided at the tip part of the insertion part of the endoscope of the first endoscope device, with a second balloon being provided at the tip part of the insertion assisting tool of the first endoscope device, a expandable and contractible third balloon which is provided at the tip part of the insertion part of the endoscope of the second endoscope device, with a fourth balloon being provided at the tip part of the insertion assisting tool of the second endoscope device, wherein the insertion parts of the endoscopes are inserted while expanding and contracting the first to fourth balloons.

According to the endoscope system of the present invention, when the image pickup device of the first endoscope device detects illumination light irradiated from the illumination device of the second endoscope device, the control device performs control so as to reduce light quantity of the illumination device of the second endoscope device based on the level of luminance signal outputted from the solid state image pickup element of the image pickup device, and when the image pickup device of the second endoscope device detects illumination light irradiated from the illumination device of the first endoscope device, the control device performs control so as to reduce light quantity of the illumination device of the first endoscope device based on the level of luminance signal outputted from the solid state image pickup element of the image pickup device, as a result of which a good observation image can be displayed on the display device without each endoscope device being influenced by the illumination light of the other endoscope device.

BRIEF DESCRIPTION OF THE DRAWINGS

FIG. 6 is a sectional side view showing the tip part of an overtube into which the insertion part is inserted; and FIGS. 7A to 7H are illustrations showing an operating method for the endoscope device shown in FIG. 1.

DETAILED DESCRIPTION OF THE PREFERRED EMBODIMENTS

The preferred embodiments of an endoscope system and an operation method for the endoscope according to the present invention are described below with reference to accompanying drawings.

Figure 1:
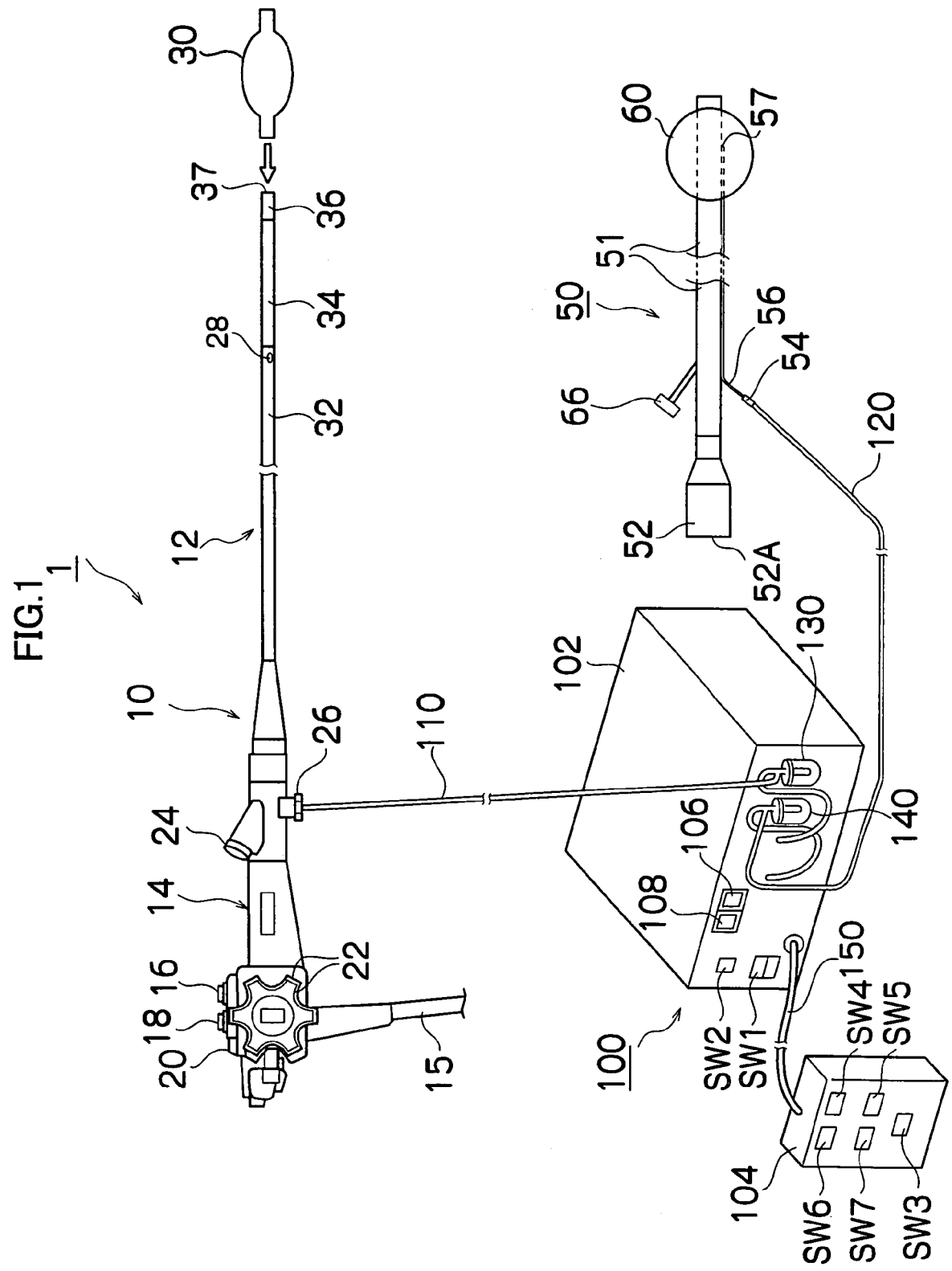
FIG. 1 is a figure showing a configuration of an endoscope device according to an embodiment of the present invention.
Figure 2:
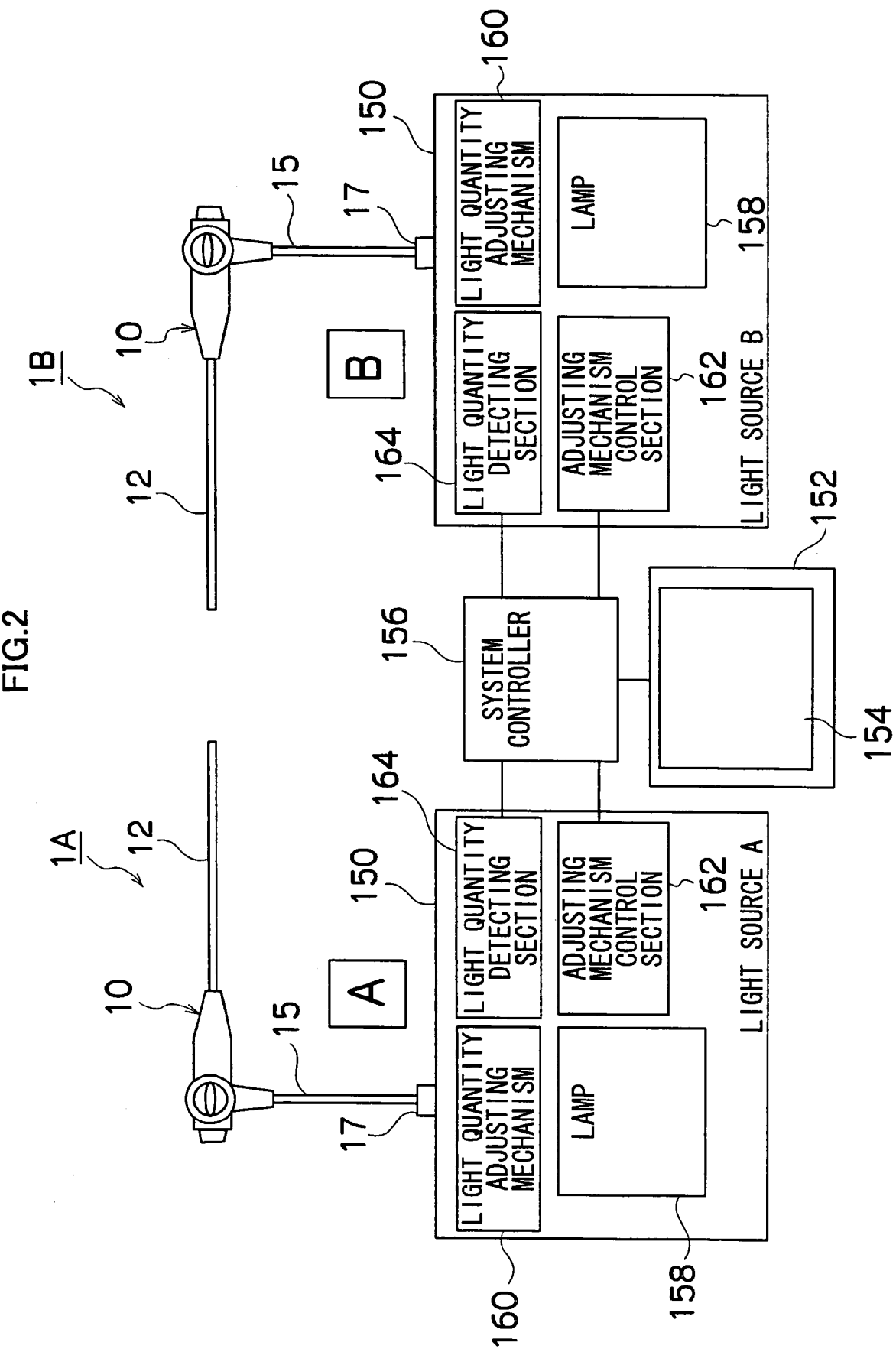
FIG. 2 is a figure showing a system configuration of an endoscope system according to an embodiment of the present invention.

FIG. 1 is a figure showing a configuration of an endoscope device of an endoscope system according to a present embodiment. The endoscope device 1 shown in the figure comprises an endoscope 10, an overtube (corresponding to an insertion assisting tool) 50, and a balloon control device 100. The endoscope system according to the embodiment is, as shown in FIG. 2, provided with two endoscope devices 1 shown in FIG. 1, in which system two endoscope devices 1, 1 are simultaneously inserted into a body cavity so as to perform treatment such as polyp excision, in cooperation with each other. In FIG. 2, an endoscope device (a first endoscope device) at the left-hand side is designated by reference character 1A, and an endoscope device (a second endoscope device) at the right-hand side is designated by reference character 1B. In FIG. 2, the overtube 50 and the balloon control device 100 are omitted in order to avoid duplication as they are shown in FIG. 1.

In FIG. 1, the endoscope 10 is provided with a hand operation part 14 and an insertion part 12 continuously connected to the hand operation part 14. A universal cable 15 is connected to the hand operation part 14, and at the tip of the universal cable 15, a connector 17 which is connected to a light source device 150 shown in FIG. 2 and to a processor (not shown), is provided. The light source device 150 will be described below.

In the hand operation part 14 in FIG. 1, an air and water supply button 16, a suction button 18, and a shutter button 20, which are operated by an operator, are arranged side by side, while a pair of angle knobs 22 and a forceps insertion section 24 are provided at predetermined positions, respectively. The hand operation part 14 is further provided with a balloon air supply port 26 for supplying and sucking air into and from a first balloon 30 in a position with no interference for the operation.

The insertion part 12 comprises a soft part 32 constituting substantially the whole length of the insertion part 12, a curved part 34 connected to the tip of the soft part 32 and a hard tip part 36 connected to the tip of the curved part 34. The curved part 34 is constituted by bendably connecting a plurality of nodal rings and is remotely and curvilinearly operated by a wire (not shown) which is pushed and pulled by rotating operation of the pair of angle knobs 22 provided for the hand operation part 14. Thereby, a tip surface 37 of the hard tip part 36 can be directed toward a desired direction, such as the observation direction of diseased part.

Figure 3:
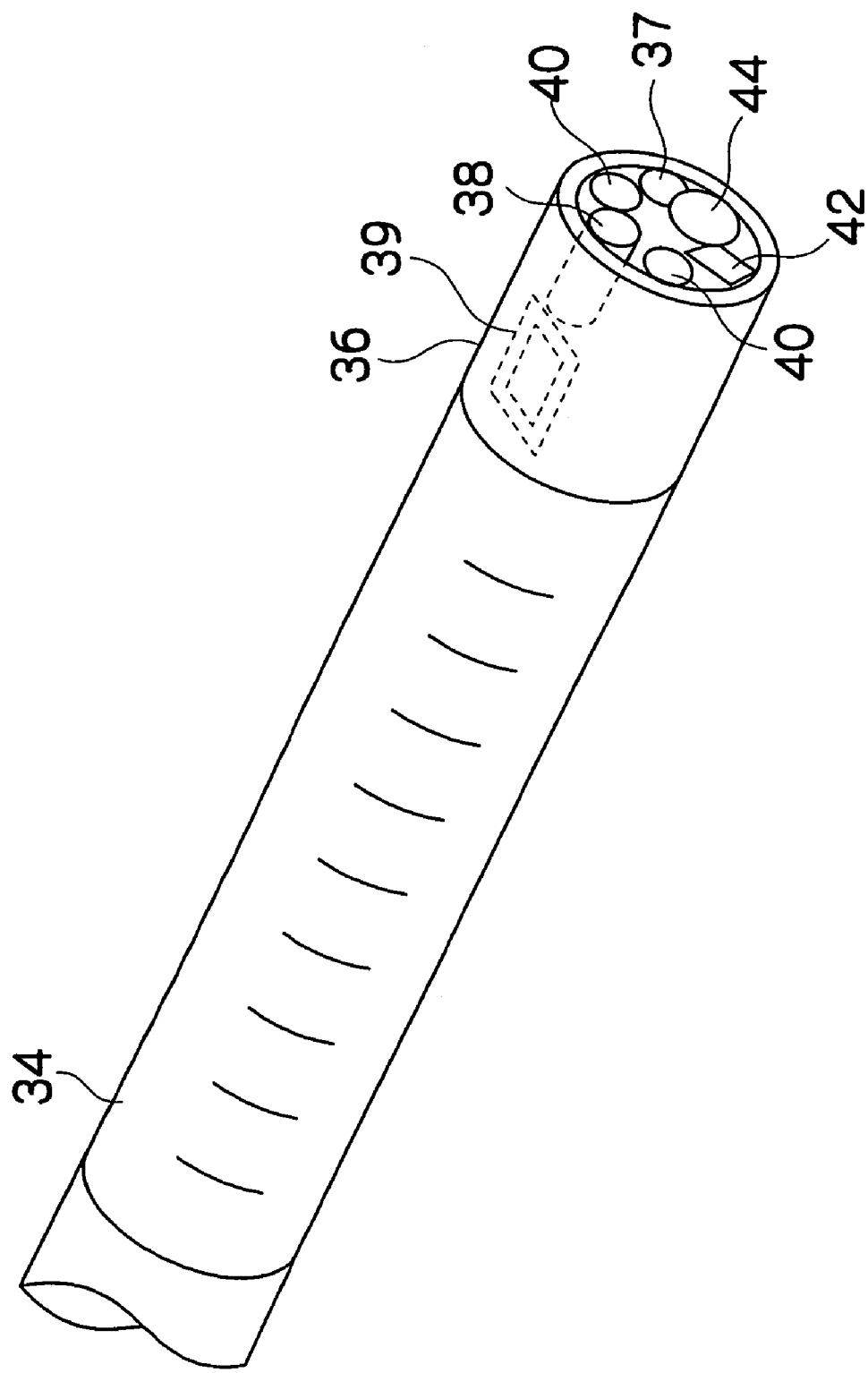
FIG. 3 is a perspective view showing a hard tip part of an insertion part of the endoscope.

As shown in FIG. 3, the tip surface 37 of the hard tip part 36 is provided with an objective optical system 38 at a slightly upper part of the central part of the tip surface. Also, illumination lenses 40 are arranged on both right and left sides of the objective optical system 38, and an air and water supply nozzle 42 and a forceps opening 44, etc. are further provided in a predetermined position under the objective optical system 38.

An observation image taken through the objective optical system 38, the optical path of which observation image is refracted by 90° by a prism (not shown), is formed on a solid state image pickup element (image pickup device) 39 arranged at an image forming position of the objective optical system 38. From the solid state image pickup element 39, an electric signal for displaying the observation image is outputted. The electric signal is transmitted to a signal line wired from the insertion part 12 through the hand operation part 14 and the universal cable 15, which are shown in FIG. 1, and outputted to a processor (not shown) through the connector 17 shown in FIG. 2. The processor is provided with a video signal processing section which performs conversion processing of the electric signal to a video signal, and outputs the video signal subjected to the conversion processing to a monitor (display device) 152. As a result, the observation image is displayed on a display screen 154 of the monitor 152.

In addition, the endoscope system according to the present embodiment is configured such that the observation images imaged by two endoscope devices 1A, 1B are displayed by the single monitor 152. For this reason, the display screen 154 of the monitor 152 is divided into two display screens and is set to display a picture of the endoscope device 1A on one of the two display screens and a picture of the endoscope device 1B on the other display screen. The size of the display screen can be properly changed by a picture size adjustment command signal from a system controller (control device) 156. For example, the display size of the observation image of a preferential endoscope device between the endoscope devices 1A and 1B can also be set to be large. The observation image of a selected endoscope device can also be fully displayed on the screen.

The system controller 156 comprises a CPU for generally controlling the whole endoscope system, and a program for performing dimming control of illumination light based on the light quantity detected by the endoscope devices 1A and 1B, i.e. on a luminance level signal outputted from the solid state image pickup element 39 is built in a ROM. A program for controlling, in accordance with a situation, the internal pressure of all the balloons which will be explained in the present embodiments is also built in the ROM.

The illumination lenses 40 shown in FIG. 3 are lenses for irradiating illumination light to an observation part. The illumination light is sent from a xenon lamp (illumination device) 158 of high-luminance built in the light source device 150 in FIG. 2 to the illumination lenses 40 via a light guide (not shown). Light quantity of the illumination light from the xenon lamp 158 is controlled so as to be reduced by a light quantity adjusting mechanism 160 such as a diaphragm device, and the size of the diaphragm aperture of the light quantity adjusting mechanism 160 is controlled by an adjusting mechanism control section 162 controlled by the system controller 156. The system controller 156 also controls the adjusting mechanism control section 162 based on a light quantity detection signal from a light quantity detecting section 164 built in the light source device 150. The light quantity detecting section 164 detects an electric signal of luminance signal level transmitted from the solid state image pickup element 39 to the processor, and the detected luminance signal level value is outputted to the system controller 156. A saturation luminance signal level value of the solid state image pickup element 39 is stored in a RAM of the system controller 156. For example, when the luminance signal level value detected at the side of the endoscope device 1A reaches a saturation luminance signal level value, the system controller 156 controls the adjusting mechanism control section 162 of the endoscope device 1B so as to make light quantity of the illumination light reduced or to make the illumination stopped at the side of the endoscope device 1B. Thereby, the observation image picked up by the endoscope 1A is displayed again on the display screen 154 of the monitor 152.

When the luminance signal level of the solid state image pickup element 39, reaches the saturation luminance signal level, the observation image is whitened on the display screen 154 in a manner that halation is generated, and becomes unable to be confirmed, but by performing control so as to reduce light quantity of the illumination light and to stop illumination, a clear observation image can be displayed again. In addition, after performing control so as to reduce light quantity of the illumination light at the side of endoscope device 1B, the adjusting mechanism control section 162 of the endoscope device 1A is controlled so as to control the light quantity adjusting mechanism 160 such that the light quantity of the endoscope device 1A becomes an appropriate value, as a result of which the optimal picture can be obtained.

Figure 4:
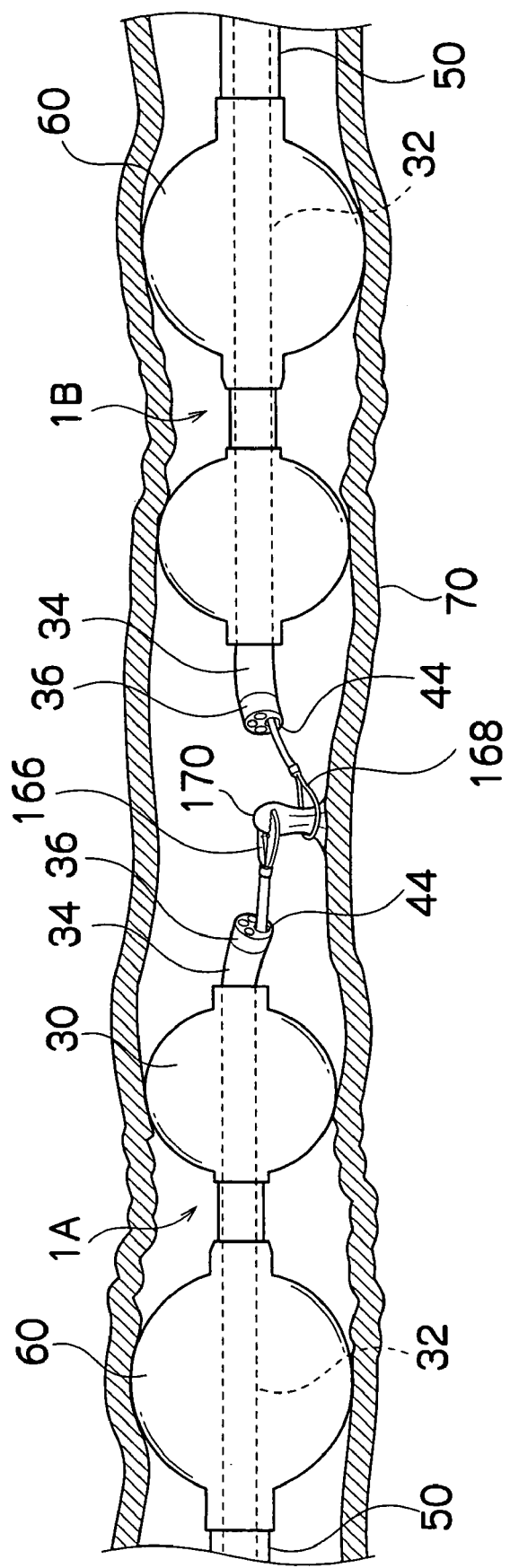
FIG. 4 is a sectional view schematically illustrating an example of treatment by means of two endoscope devices.

From the forceps opening 44 shown in FIG. 3, forcipes 166, 168 are projected as shown in FIG. 4, so as to be used for, e.g. excising a polyp 170 developed on the inner wall surface of the small intestine 70. The forceps 166 is a clamping forceps for pinching the head of the polyp 170, and forceps 168 is snare forceps for excising the entrapment of the polyp 170 with a loop-shaped wire. The forceps 166 is inserted from the forceps insertion section 24 of the endoscope device 1A, and the forceps 168 is inserted from the forceps insertion section 24 of the endoscope device 1B. Although there may be a case where an endoscope for two channel treatment is used so as to enable the forcipes 166, 168 to be used by one endoscope device, in the present embodiment, forceps 166 is used by the endoscope device 1A, and forceps 168 is used by the endoscope device 1B. An example of treatment shown in FIG. 4 is the case where the endoscope device 1A is inserted from the anus, and the endoscope device 1B is inserted from the mouth, each being made to be inserted into the deep part so as to be operated in cooperation with each other. The treatment position is not limited to the small intestine 70, but a polyp developed in the caecum and the ascending colon can also be treated by the present endoscope system. Such treatment in the deep part of the intestine using two endoscope devices 1A, 1B is possible because both endoscope devices 1A, 1B are double balloon type endoscope devices.

Hereafter, the double balloon type endoscope device will be described.

As shown in FIG. 1, an air supply/suction port 28 is formed at a tip outer peripheral face of the soft part 32, and the air supply/suction opening 28 is communicated with the balloon air supply port 26 via an air supply tube (not shown) with an inner diameter of about 0.8 mm, inserted into the insertion part 12. Accordingly, when air is supplied to the balloon air supply port 26, air is blown off from the air supply/suction port 28, and conversely, when air is sucked from the balloon air supply port 26, air is sucked from the air supply/suction port 28.

Figure 5:
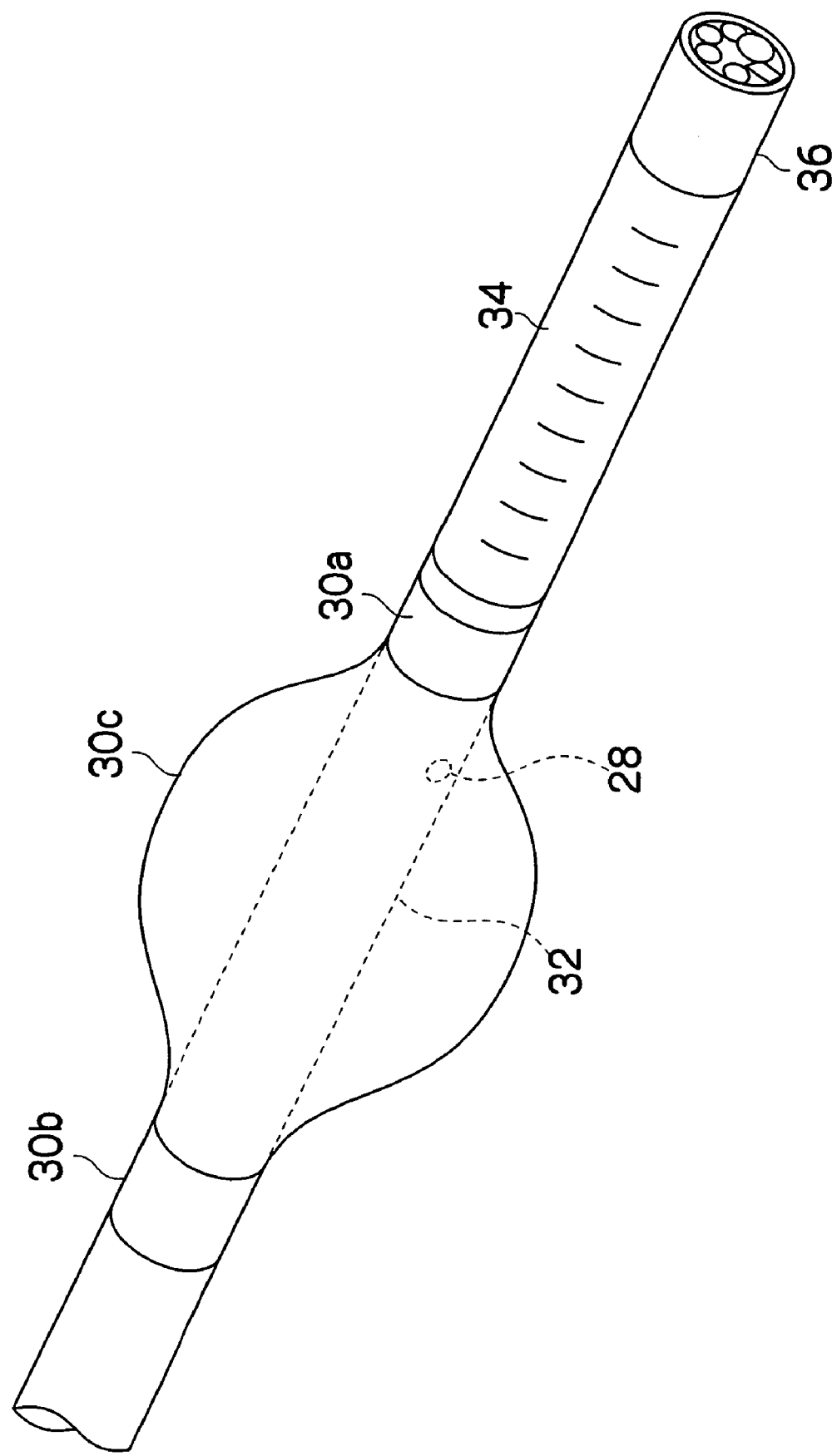
FIG. 5 is a perspective view showing the tip of the insertion part provided with a first balloon.

As shown in FIG. 5, the first balloon 30 made of an elastic material such as rubber is removably mounted at the tip of the soft part 32. The first balloon 30 is formed of a central swelled part 30C and attaching parts 30A, 30B of the both ends of the central swelled part, and is mounted to the side of the soft part 32 such that the air supply/suction port 28 is positioned within the swelled part 30C. The attaching parts 30A, 30B formed into a diameter smaller than the diameter of the soft part 32 are, after being brought into close contact with the soft part 32 with their resilient force, firmly fixed to the external peripheral surface of the soft part 32 by a band member (not shown). In the mounted first balloon 30, the swelled part 30C is swelled in an approximately spherical shape by air supplied from the air supply/suction port 28. On the contrary, by sucking air from the air supply/suction port 28, the swelled part 30C is contracted so as to be brought into close contact with the external peripheral surface of the soft part 32. In this way, by mounting the first balloon 30 to the tip of the soft part 32, as shown in FIG. 4, the first balloon 30 can be brought into close contact with the intestinal wall, so as to enable the tip end posture of the soft part 32 to be stabilized. Thereby, the hard tip part 36 can be stabilized in a desired direction by curving operation of the curved part 34.

The overtube 50 shown in FIG. 1 is formed of a tube body 51 and a gripping part 52. As shown in FIG. 6, the tube body 51 is formed into a cylindrical shape having an inner diameter slightly larger than the outer diameter of the insertion part 12. The tube body 51 is formed of a flexible urethane resin molding, of which external peripheral surface is provided with a lubricating coat and of which inner peripheral surface is also provided with a lubricating coat. A hard gripping part 52 shown in FIG. 1 is fitted to the tube body 51 in a watertight state, and the gripping part 52 is detachably connected to the tube body 51. The insertion part 12 is inserted from a base end opening part 52A of the gripping part 52 to the tube body 51. Reference numeral 66 designates a supply port for supplying lubricating water into the tube body 51.

As shown in FIG. 1, a balloon air supply port 54 is provided at the base end side of the tube body 51. The balloon air supply port 54 is connected with an air supply tube 56 with the inner diameter of about 1 mm, which tube is adhered to the external peripheral surface of the tube body 51 and extended to near a tip part 58 of the tube body 51, as shown in FIG. 6.

The tip part 58 of the tube body 51 is formed to be a tapered shape in order to prevent entanglement of the intestinal wall, etc. The base end side of the tip part 58 of the tube body 51 is fitted with a second balloon 60 formed of a elastic body, such as rubber. The second balloon 60 is fitted in a state of being penetrated by the tube body 51, and comprises a central swelled part 60C and attaching parts 60A, 60B of the both ends of the central swelled part. The attaching part 60A is folded to the inside of the swelled part 60C, and the folded attaching part 60A is wound with an X-ray contrast thread 62 so as to be fixed to the tube body 51. The attaching part 60B at the side of the base end is arranged outside the second balloon 60, and is wound with a thread 64 so as to be fixed to the tube body 51.

The swelled part 60C is formed to be an approximately spherical shape in a natural state (state with no expansion and contraction), and the size of the swelled part 60C is formed larger than the size of the first balloon 30 in a natural state (state with no expansion and contraction). Accordingly, when air is supplied to the first balloon 30 and the second balloon 60 at the same pressure, the outer diameter of the swelled part 60C of the second balloon becomes larger than the outer diameter of swelled part 30C of the first balloon 30. For example, when the outer diameter of the first balloon 30 is φ25 mm, the outer diameter of the second balloon 60 is configured to be φ50 mm.

The above described tube 56 is opened within the swelled part 60C to form an air supply/suction port 57. Thus, when air is supplied from the balloon air supply port 54, air is blown off from the air supply/suction port 57, so as to expand the swelled part 60C. Also, when air is sucked from the balloon air supply port 54, air is sucked from the air supply/suction port 57, so as to contract the second balloon 60.

On the other hand, the balloon control device 100 in FIG. 1 is a device for supplying and sucking fluid such as air to and from the first balloon 30, and for supplying and sucking fluid such as air to and from the second balloon 60. The balloon control device 100 comprises a device body 102 provided with a pump, a sequencer, etc. (not shown), and a hand switch 104 for remote control.

In the front panel of the device body 102, there are provided a power switch SW1, a stop switch SW2, a pressure indicator 106 for the first balloon 30, and a pressure indicator 108 for the second balloon 60. Also, in the front panel of the device body 102, there are mounted a tube 110 for supplying and sucking air to and from the first balloon 30, and a tube 120 for supplying and sucking air to and from the second balloon 60. In the middle of each of the tubes 110, 120, there are provided liquid storage tanks 130, 140 for storing the body fluid backward flowing from the first and second balloons, in case of breakage of the first and second balloons, respectively.

On the other hand, for the hand switch 104 there are provided a stop switch SW3 similar to the stop switch SW2 at the side of the device body 102, an ON/OFF switch SW4 for causing pressurization/depressurization of the first balloon 30, a pause switch SW5 for keeping pressure of the first balloon 30, an ON/OFF switch SW6 for causing pressurization/depressurization of the second balloon 60 and a pause switch SW7 for keeping pressure of the second balloon 60. The hand switch 104 is electrically connected to the device body 102 via a cable 150.

The balloon control device 100 constituted in this way, supplies air to the first balloon 30 and the second balloon 60 to expand them, and controls the air pressure to a fixed value to keep the first balloon 30 and the second balloon 60 in the expanded state. The balloon control device 100 also sucks air from the first balloon 30 and the second balloon 60 to contract them, and controls the air pressure to a fixed value to keep the first balloon 30 and the second balloon 60 in the contracted state.

Next, the operation method of the endoscope device 1B inserted from the mouth of a patient is explained with reference to FIGS. 7A to 7H.

First, as shown in FIG. 7A, in a state where the overtube 50 covers the insertion part 12, the insertion part 12 is inserted into the small intestine (for example, the duodenum descending limb) 70. At this time, the first balloon 30 and the second balloon 60 are contracted.

Then, as shown in FIG. 7B, in a state where the tip part 58 of the overtube 50 is inserted to a bent part of the intestinal canal 70, the second balloon 60 is supplied with air so as to be expanded. Thereby, the second balloon 60 is stopped by the intestinal canal 70, and the tip part 58 of the overtube 50 is fixed to the intestinal canal 70.

Next, as shown in FIG. 7C, only the insertion part 12 of the endoscope 10 is inserted into the deep part of the small intestine 70. Then, as shown in FIG. 7D, the first balloon 30 is supplied with air so as to be expanded. Thereby, the first balloon 30 is fixed to the small intestine 70. Since the size of the first balloon at the time of expansion is smaller than that of the second balloon 60, the first balloon 30 imposes a small amount of burden on the small intestine 70, so as to enable the damage of the small intestine 70 to be prevented.

Subsequently, after contracting the second balloon 60 by sucking air therefrom, as shown in FIG. 7E, the overtube 50 is pushed in so as to be inserted along the insertion part 12. Then, after the tip part 58 of the overtube 50 is pushed in near the first balloon 30, as shown in FIG. 7F, the second balloon 60 is supplied with air so as to be expanded. Thereby, the second balloon 60 is fixed to the small intestine 70. That is, the small intestine 70 is grasped by the second balloon 60.

Next, the overtube 50 is pulling in as shown in FIG. 7G. Thereby, the small intestine 70 is contracted substantially straightly so that excessive deflection and bending of the overtube 50 are eliminated. When the overtube 50 is pulled in, both the first balloon 30 and the second balloon 60 are restrained by the small intestine 70, but the frictional resistance of the first balloon 30 is smaller than the frictional resistance of the second balloon 60. Accordingly, even when the first balloon 30 and the second balloon 60 are moved so as to be relatively separated from each other, since the first balloon 30 with a small frictional resistance slides with respect to the small intestine 70, the small intestine 70 is not damaged by being pulled by both the balloons 30, 60.

Subsequently, as shown in FIG. 7H, air is sucked from the first balloon 30 so as to contract the first balloon 30. The hard tip part 36 of the insertion part 12 is then inserted into the deep part of the small intestine 70 as much as possible. That is, the insertion operation shown in FIG. 7C is performed again. Thereby, the hard tip part 36 of the insertion part 12 can be inserted into the deep part of the small intestine 70. In the case where the insertion part 12 is further inserted into the deep part, following the fixing operation as shown in FIG. 7D, the pushing-in operation as shown in FIG. 7E, the grasping operation as shown in FIG. 7F, the pulling-in operation as shown in FIG. 7G and the inserting operation as shown in FIG. 7H, may be repeatedly performed in this order. Thereby, the insertion part 12 can be further inserted into the deep part of the small intestine 70, and as shown in FIG. 4, the hard tip part 36 of the insertion part 12 can be located in the targeted deep part of the small intestine.

On the other hand, the insertion part 12 of the endoscope device 1A inserted from the anus of the patient is also inserted into the deep part by the same operation method as the endoscope device 1B, so as to enable the hard tip part 36 to be located in the targeted deep part of the small intestine via the rectum and the large intestine. At this time, both of the second balloons 60 (the second balloon for the endoscope device 1A, the fourth balloon for the endoscope device 1B) are expanded so as to assure the treatment space, and both of the first balloons 30, 30 (the first balloon for the endoscope device 1A, the third balloon for the endoscope device 1B) are expanded so as to enable the hard tip part 36 of the insertion part 12 to be stably directed to a desired direction by the curved part 34.

Incidentally, in the case where a same diseased part is treated by both the endoscope devices 1A, 1B, as shown in FIG. 4, when the solid state image pickup element 39 of the endoscope device 1A detects illumination light from the xenon lamp 158, which is irradiated from the illumination lens 40 of the endoscope device 1B, the system controller 156 performs control so as to reduce light quantity of the xenon lamp 158 of the endoscope device 1B based on the level of luminance signal outputted from the solid state image pickup element 39 of the endoscope device 1A. That is, when a signal of the saturation luminance level is outputted from the solid state image pickup element 39 of the endoscope device 1A, the light quantity adjusting mechanism 160 performs control so as to reduce light quantity of the illumination light from the xenon lamp 158 of the endoscope device 1B. Then, the adjusting mechanism control section 162 of the endoscope device 1A is controlled, so that the light quantity adjusting mechanism 160 is controlled to allow light quantity of the endoscope device 1A to become an appropriate value, thereby enabling an optimum picture of the endoscope device 1A to be obtained.

Also, when the solid state image pickup element 39 of the endoscope device 1B detects illumination light from the xenon lamp 158, which is irradiated from the illumination lens 40 of endoscope device 1A, the system controller 156 performs control so as to reduce light quantity of the xenon lamp 158 of the endoscope device 1A based on the level of luminance signal outputted from the solid state image pickup element 39 of the endoscope device 1B. That is, when a signal of the saturation luminance level is outputted from the solid state image pickup element 39 of the endoscope device 1B, the light quantity adjusting mechanism 160 performs control so as to reduce light quantity of the illumination light from the xenon lamp 158 of the endoscope device 1A. Then, the adjusting mechanism control section 162 of the endoscope device 1B is controlled, so that the light quantity adjusting mechanism 160 is controlled to allow light quantity of the endoscope device 1B to become an appropriate value, thereby enabling an optimum picture of the endoscope device 1B to be obtained.

Consequently, according to the endoscope system of the present embodiment, a good observation image can be displayed in the monitor 152 without each of the endoscope devices 1A, 1B being influenced by the illumination light of the other endoscope device.

The light quantity of the illumination light to be reduced, which is not restricted in particular, may be set in accordance with the dynamic range of the solid state image pickup element 39. The dimming control may also be performed so as to stop the illumination light. In this case, it is preferred to specify in the system controller 156 the endoscope device having priority, such that the illumination light of the endoscope device having priority is not stopped and the illumination light of the endoscope device without priority is stopped.

What is claimed is:

1. An endoscope system, comprising:
a first endoscope device provided with a first endoscope in which a first illumination device, a first image pickup device and a first balloon are attached to a tip part of a first insertion part of the first endoscope, and with a first insertion assisting tool into which the first insertion part of the first endoscope is inserted, said first insertion assisting tool assists insertion of the first insertion part into a body cavity and has a first insertion assisting tool tip part to which a second balloon is attached;
a second endoscope device provided with a second endoscope in which a second illumination device, a second image pickup device and a third balloon are attached to a tip part of a second insertion part of the second endoscope, and with a second insertion assisting tool into which the second insertion part of the second endoscope is inserted, said second insertion assisting tool assists insertion of the second insertion part into a body cavity and has a second insertion assisting tool tip part to which a fourth balloon is attached;
a display device for displaying an object image photographed by the first image pickup device of the first endoscope device and the second image pickup device of the second endoscope device; and
a control device for controlling a light quantity of the second illumination device, based on a level of luminance signal outputted from a first solid state image pickup element of the first image pickup device, when the first image pickup device detects illumination light irradiated from the second illumination device of the second endoscope device, or for controlling a light quantity of the first illumination device, based on a level of luminance signal outputted from a second solid state image pickup element of the second image pickup device, when the second image pickup device of the second endoscope device detects illumination light irradiated from the first illumination device of the first endoscope device,
wherein the control device performs control so as to reduce light quantity of the second endoscope device when the luminance signal level from the first solid state image pickup element of the first endoscope device reaches a saturation luminance signal level, or performs control so as to reduce light quantity of the first endoscope device when the luminance signal level from the second solid state image pickup element of the second endoscope device reaches a saturation luminance signal level.

* * * * *

UNITED STATES PATENT AND TRADEMARK OFFICE
CERTIFICATE OF CORRECTION

PATENT NO. : 7,585,276 B2
APPLICATION NO. : 11/068433
DATED : September 8, 2009
INVENTOR(S) : Hiromu Itoi It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1224 days.

Signed and Sealed this

Fourteenth Day of September, 2010

David J. Kappos
*Director of the United States Patent and Trademark Office*